United States Patent
Omairi et al.

(10) Patent No.: US 7,389,705 B2
(45) Date of Patent: Jun. 24, 2008

(54) LANDFARMING SIMULATION TESTING APPARATUS AND METHOD

(75) Inventors: Rashed S. Omairi, Dammam (SA); Mariam H. Al-Soufi, Dammam (SA)

(73) Assignee: Saudi Arabian Oil Company (SA)

( * ) Notice: Subject to any disclaimer, the term of this patent is extended or adjusted under 35 U.S.C. 154(b) by 345 days.

(21) Appl. No.: 11/196,030

(22) Filed: Aug. 3, 2005

(65) Prior Publication Data
US 2006/0029521 A1 Feb. 9, 2006

Related U.S. Application Data

(60) Provisional application No. 60/598,276, filed on Aug. 3, 2004.

(51) Int. Cl.
*G01N 17/00* (2006.01)
(52) U.S. Cl. .................................................. 73/865.6
(58) Field of Classification Search ................ 73/865.6
See application file for complete search history.

(56) References Cited

U.S. PATENT DOCUMENTS

| | | | |
|---|---|---|---|
| H229 H | 3/1987 | Phillips | |
| 4,668,388 A | 5/1987 | Dibble et al. | |
| 4,750,355 A | 6/1988 | Urabe et al. | |
| 4,817,039 A | 3/1989 | Frost | |
| 5,323,662 A * | 6/1994 | Lahoda | 73/866 |
| 5,458,747 A | 10/1995 | Marks et al. | |
| 5,739,031 A | 4/1998 | Runyon | |
| 5,854,061 A * | 12/1998 | Horn et al. | 435/262.5 |
| 5,942,682 A | 8/1999 | Ghetzler et al. | |
| 6,023,985 A | 2/2000 | Fournier | |
| 6,461,510 B1 | 10/2002 | Boles et al. | |
| 6,772,536 B2 * | 8/2004 | Ely et al. | 34/380 |

FOREIGN PATENT DOCUMENTS

| | | | |
|---|---|---|---|
| JP | 2003047340 | * | 2/2003 |
| JP | 2003225647 | | 8/2003 |
| WO | WO 9712511 | | 4/1997 |

OTHER PUBLICATIONS

GEA Kestner Forced Circulation Evaporator, website printout, 3 pages, Oct. 18, 2005.

* cited by examiner

*Primary Examiner*—Robert R Raevis
(74) *Attorney, Agent, or Firm*—Bracewell & Giuliani LLP

(57) ABSTRACT

An apparatus and method for studying the effect of heat, wind and other physical and/or biological factors on the loss of hydrocarbons from oily sludge wastes in a landfarming system. Preferably, the invention is a landfarming simulation testing apparatus and method that can be used to simulate real environmental conditions in a laboratory. The invention may be used to study the effect of physical factors such as, for example, temperature, wind, humidity, sunrays and/or acid rain. Also, the invention can be used to study the effect of biological factors such as, for example, oily sludge-degrading microorganisms. The apparatus is also useful for treatment of appropriate amounts of waste.

12 Claims, 1 Drawing Sheet

LANDFARMING SIMULATION TESTING APPARATUS AND METHOD

RELATED APPLICATIONS

This application claims benefit from U.S. Provisional Application No. 60/598,276, filed Aug. 3, 2004.

TECHNICAL FIELD OF THE INVENTION

The present invention relates to landfarming, and more particularly, to an apparatus and method for simulating environmental conditions in a laboratory setting in order to observe the effects of physical and/or biological factors on oily sludge waste degradation in a landfarming system.

BACKGROUND OF THE INVENTION

Oily sludge is one of the primary industrial wastes generated in connection with crude oil production. A large amount of oily sludge is generated each year by the oil industry. The main source of the oily sludge is tank bottoms. Other potential sources of oily sludge include oil-water separators, operating slops, oil spills and operating residues.

Petroleum refiners have utilized a variety of means for treating or disposing of this oily sludge waste. One such means is landfarming. Landfarming is an aboveground remediation technology for reducing concentrations of oily sludge and other petroleum waste product constituents in soil. Landfarming typically involves mixing a petroleum waste product with a thin layer of soil on the ground surface, and then stimulating biodegradation of the mixture. Biodegradation is a microbial treatment of the soil and petroleum mixture through aeration and/or the addition of minerals, nutrients, and moisture. The treatment results in enhanced microbial activity, which causes degradation of the petroleum product constituents.

The petroleum products treated in a landfarming system typically include components that are volatile, such as gasoline, components that are nonvolatile, such as heating and lubricating oils, and components that fall somewhere in between, such as kerosene and diesel fuel. In general, a petroleum product can contain more than one hundred different constituents that possess a wide range of volatility. During landfarming, the lighter, more volatile petroleum products tend to evaporate out. The mid-range products contain lower percentages of lighter, more volatile constituents, and biodegradation of these petroleum products is more significant than evaporation. Heavier, nonvolatile petroleum products generally do not evaporate out during landfarming, and the dominant mechanism that breaks down these petroleum products is biodegradation. Generally, the higher the molecular weight of the nonvolatile petroleum constituent, the longer the period of time required to break down the constituent.

It is highly desirable for researchers to be able to study the effect of one or more physical or biological factors, for example, temperature, wind and/or microorganisms, on the evaporation and/or biodegradation of oily sludge and other petroleum waste treated in a landfarming system. This type of study, however, has traditionally only been possible at the actual physical location of the landfarming system. As such, researchers have been limited as to the extent to which they could alter temperature and environmental conditions without disturbing the physical surroundings and/or the landfarming process. Further, attempts to produce desired temperature or environmental conditions at actual locations for experimental purposes have proven to be costly and inefficient.

Therefore, the art has sought an apparatus or method for simulating real environmental conditions in a laboratory setting which allows researchers to study the effect of various physical and biological factors on the overall diminution of oily sludge hydrocarbons in a landfarming system and is efficient and cost effective The present invention is used in the field of oily sludge waste management. The apparatus and method of the present invention is used to study the affect of heat, temperature, wind speed and other physical and biological factors on the loss or degradation of oily sludge hydrocarbons in a landfarming system.

SUMMARY OF THE INVENTION

The present invention relates to an apparatus and method for studying the effect of heat, wind and other physical and/or biological factors on the loss of hydrocarbons from oily sludge wastes in a landfarming system. Preferably, the invention is a landfarming simulation testing apparatus and method that can be used to simulate real environmental conditions in a laboratory. The invention may be used to study the effect of physical factors such as, for example, temperature, wind, humidity, sunrays and/or acid rain. Also, the invention can be used to study the effect of biological factors such as, for example, oily sludge-degrading microorganisms. Other physical and biological factors may also be studied, as would be recognized to those skilled in the art. The apparatus is also useful for treatment of appropriate amounts of waste.

In one embodiment, the apparatus will be used to treat a soil sample specimen containing oily sludge waste, and will include a chamber having a storage area therein sufficient to hold one or more specimen containers, a heat source for providing heat to the apparatus and an air source for supplying air to the apparatus. Degradation of the oily sludge hydrocarbons is initiated in the chamber through exposure to the heat source and air source. The apparatus also preferably includes means for extracting the oily sludge hydrocarbons from the soil specimen operable to measure degradation of the oily sludge hydrocarbons. In one embodiment, the means for extracting the oily sludge hydrocarbons from the soil specimen is connected to or in communication with the chamber. In an alternate embodiment, the means for extracting the oily sludge hydrocarbons from the soil specimen is separate from the chamber.

The chamber may be enclosed or at least partially exposed to the environment. The apparatus can also include a pressure regulator for regulating the pressure of air in the apparatus. A solenoid valve or other means can be used for controlling the automatic opening and closing of the air supply to the apparatus. A temperature indicator can be used for displaying the present temperature in the apparatus and/or of the sample material. A control valve can be used for controlling the flow of supply air to the apparatus. A timer can be used for controlling the timing of the air supply to the system. A plurality of air dampers can be used for regulating the flow of air to the apparatus. A temperature controller that is in communication with at least the temperature indicator can be used for automatically controlling the temperature in the apparatus and/or of the sample material.

In one aspect, this invention can be used to investigate the loss of oily sludge hydrocarbons via an abiotic mechanism, for example, volatilization or evaporation, in a landfarming system. In another aspect, this invention may be used to investigate the loss of oily sludge hydrocarbons via a biotic mechanism, for example, biodegradation. In another aspect, the present invention can be used to study the loss of oily sludge hydrocarbons as a result of both biotic and abiotic mechanisms. For example, the oily sludge hydrocarbons lost from sludge samples via evaporation can be compared with those lost via a biodegradation process carried on by oily sludge degrading microorganisms.

In a preferred embodiment, a water source is used to control the moisture level of the containers. Preferably, the apparatus contains means for measuring data, including but not limited to temperature, pressure, air flow, moisture content, time, light exposure and/or degradation of the oily sludge hydrocarbons. Degradation of the oily sludge can be measured by methods known by those skilled in the art.

BRIEF DESCRIPTION OF THE DRAWINGS

So that the manner in which the features, advantages and objects of the invention, as well as others that will become apparent, may be understood in more detail, more particular description of the invention briefly summarized above may be had by reference to the embodiment thereof that are illustrated in the appended drawings, which form a part of this specification. It is to be noted, however, that the drawings illustrate only a preferred embodiment of the invention and are therefore not to be considered limiting of the invention's scope as it may admit to other equally effective embodiments.

DETAILED DESCRIPTION

Figure 1:
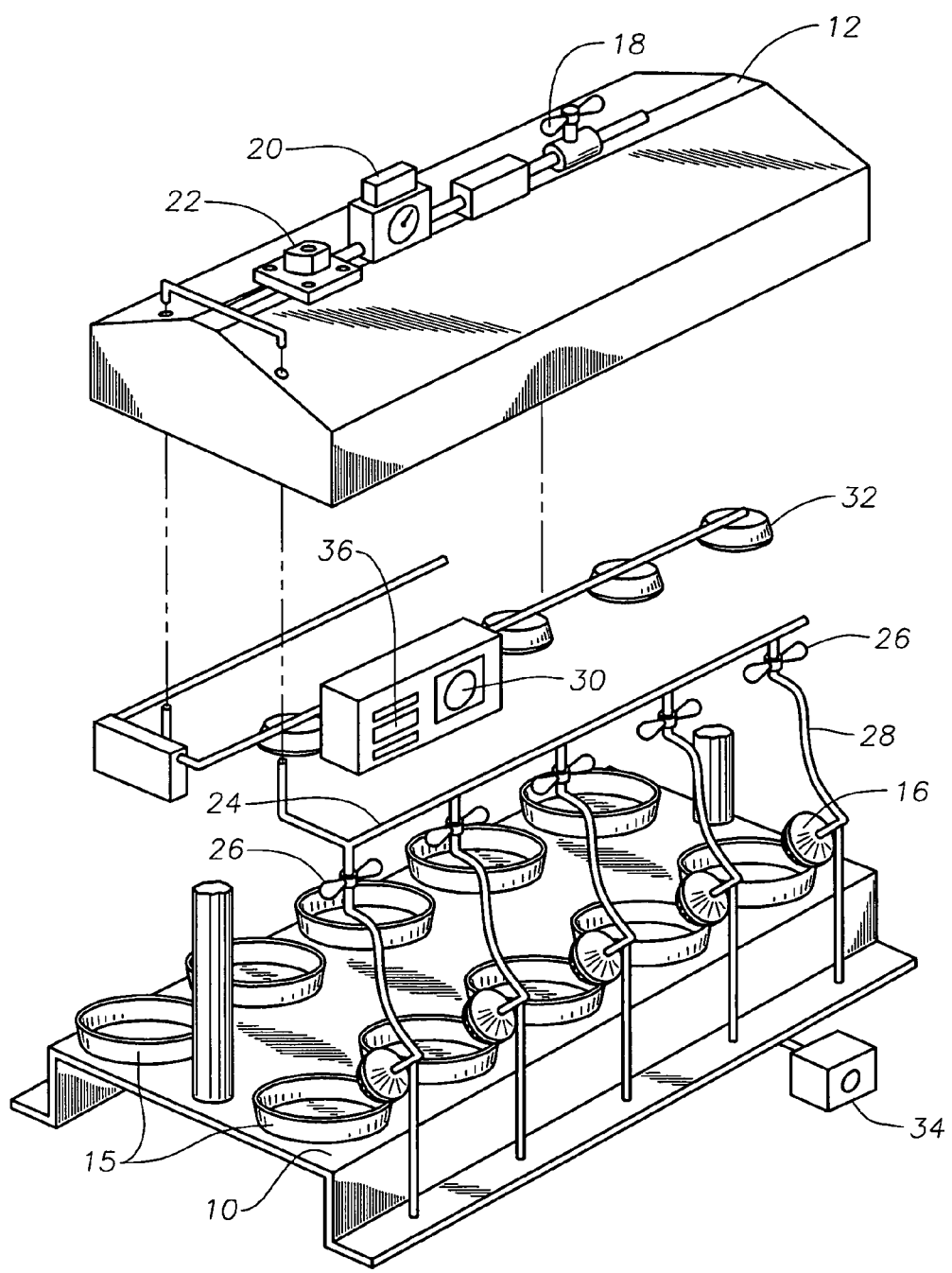
FIG. 1 is a perspective view of a preferred embodiment of the landfarming simulation testing apparatus of the present invention.

With reference to FIG. 1, a preferred embodiment of the landfarming simulation testing apparatus of the present invention is described. The apparatus includes a platform 10 that is at least partially covered by a hood 12. The platform 10 and the hood 12 generally form the boundaries of a chamber with a storage area therein defining an experimental environment. One or more specimen containers 15 can be placed on the platform 10 and arranged in a desired fashion. Alternatively, the specimen containers 15 are affixed to the platform 10 and immovable. According to one embodiment, each specimen container 15 can contain a soil sample having a predetermined level of oily sludge or other petroleum waste product; however, in other embodiments, it is not required that each container 15 contain a soil sample. Preferably, one or more of the soil samples in the containers 15 may be used as a control group, and will not contain any waste product. Alternatively, each sample can contain waste products. The soil samples can contain various levels of moisture. The soil samples can be non-stirred or stirred.

A plurality of air dampers 16 may be arranged adjacent to the platform 10. In the embodiment shown in FIG. 1, five air dampers 16 are arranged in a row along one side of the platform 10. In an alternative embodiment, the platform 10 has ten air dampers 16, positioned in two parallel rows of five on opposite sides of the platform 10. An air source, for example, a compressor, supplies air to the air dampers 16. In the preferred embodiment illustrated in FIG. 1, a control valve 18 controls the amount of air delivered to the plurality of dampers 16 from the air source. A pressure regulator 20 regulates the pressure of the air supplied to the plurality of dampers 16. A solenoid valve 22 regulates airflow to the plurality of dampers 16. Air is delivered to the plurality of dampers 16 via a common header 24. Preferably, each damper 16 has a corresponding segment of piping that extends from the header 24. Each segment of piping extending from the header 26 has a valve 26 that can be used to regulate airflow to the damper 16. Airflow passes through lengths of flexible hosing 28 that connect the segments of piping to the dampers 16.

The air dampers 16 are used to distribute air to the soil specimens on the platform 10. The purpose of the airflow is to simulate wind, as would be encountered by the soil samples under standard outdoor conditions. For example, a high rate of airflow from the dampers 16 would be used to replicate a windstorm or hurricane. Preferably, the distance between each air damper 16 in a row is identical. Similarly, the distance between each damper 16 and the closest corresponding specimen container 15 is preferably identical. This is to ensure that identical flow of air can be provided to each soil sample, if desired. In one embodiment, a timer 30 can be used to control the airflow from the dampers 16. The timer 30 can be automatic, or alternatively, it can be operated manually.

In a preferred embodiment, a heat source can be attached to the apparatus. In the preferred embodiment shown in FIG. 1, a plurality of infrared heat lamps 32 are aligned in a single row and affixed to the hood 12 of the apparatus. The lamps 32 provide heat to the soil samples on the platform 10. The heat produced by the lamps 32 is meant to simulate the ambient temperature that the soil samples would experience under standard outdoor conditions. Preferably, the distance between each infrared heat lamp 32 in the row is identical. Similarly, the distance between each lamp 32 and the closest corresponding soil sample container 15 is preferably identical. This is to ensure that the similar temperature conditions can be provided for each sample on the platform 10, if desired.

A temperature controller 34 may be used to control the intensity of the heat produced by the heat lamps 32. There can be an individual temperature controller 34 for each of the lamps 32, or alternatively, the lamps 32 can all be regulated by one controller 34. A temperature indicator 36 can be used to display the temperature of the soil samples. Further, the temperature indicator 36 can be used to display the ambient temperature within the apparatus. The temperature controller 34 can be operated manually, or alternatively, it can operate automatically. For example, a researcher may wish to set the temperature controller 34 to automatically adjust temperature within the apparatus to simulate an outdoor temperature change from daylight to nighttime, or from summer to winter.

Embodiments of the apparatus of the present invention have been used in two experimental studies. In the first study, researchers evaluated the optimum conditions for the treatment of the oily sludge collected from an open storage pit at a marine area in a refinery by the landfarming method using laboratory and field techniques. In the second study, researchers evaluated landfarming as a method to treat waste oily sludge deposited in 20 pits adjacent to a refinery facility. The studies determined optimum treatment conditions in the apparatus of the invention, rates of hydrocarbon biodegradation and process performance. An objective in both studies was to compare the overall loss of hydrocarbons in contaminated soil via both abiotic and biotic mechanisms.

In one embodiment, the apparatus and method of the present invention can be used to study the effect of temperature and wind conditions on hydrocarbons from oily sludge samples in landfarming systems. In another embodiment, the apparatus and method of the present invention can be used to study the effect of biodegradation on oily sludge hydrocarbons in a landfarming system. In another embodiment, the apparatus and method of the present invention can be used to investigate the ability of specific microbial species to degrade oily sludge samples in a landfarming system. Preferably, more than one study will be carried out simultaneously, since the apparatus of the present invention is capable of handling ten samples at the same time in a preferred embodiment. Thus, each air damper 16 and heat lamp 32 may be set and adjusted individually in order to provide different environmental conditions for different soil samples in a preferred embodiment.

In one embodiment, the apparatus and method of the present invention can be used in connection with research on oily sludge waste that is exposed to environmental conditions while being stored in a storage area or facility. In another embodiment, the apparatus and method of the present invention can be used in connection with research on oily sludge waste that is exposed to environmental conditions during transport from one location to another, for example, form a storage area to a treatment area. In still another embodiment, the apparatus and method of the present invention may be utilized in connection with research on oily sludge waste that is exposed to environmental conditions while undergoing landfarming. It would be understood by those skilled in the art that the apparatus and method of the present invention could also be utilized in connection with research on oily sludge waste that is treated by other treatment technologies besides landfarming, for example, centrifugation or treatment in a bioreactor. In one embodiment, the oily sludge degradation can be assessed by gas chromatography (GC) analyses. Preferably, samples are dissolved in methylene chloride and auto-injected using an injection volume of 0.2 μl, an injector temperature of 300 degrees C., and a split ratio of 100:1. The oily material is preferably extracted from the soil samples using a pressure flow extraction apparatus. The organic solvent (MAC solvent) is prepared by mixing methanol, acetone, and chloroform (15:15:70). The soluble organic material recovered from the extraction procedure is then submitted for deasphaltening to remove the asphaltene fraction. Excess n-pentane is preferably added to the sample to precipitate asphaltene, which is insoluble in n-pentane. The maltene (asphaltene-free fraction) is then separated into the saturate, aromatic and resin fractions by SARA (saturated hydrocarbons, aromatic hydrocarbons, resins and asphaltene fractions)-HPLC. All fractions are then evaporated to remove the solvent and weighed to determine the weight percentage of each SARA fraction. The samples are then analyzed by GC.

The degree of biodegradation is determined using the ratios of n-C17 to pristane and n-C18 to phytane. The ratio of the two compound classes n-C17/Pr and n-C18/Ph is used to estimate the relative degree of degradation. When the values of these two ratios decrease, it indicates that n-C17 and n-C18 are being biodegraded because multi-branched acyclic isoprenoids (pristane and phytane) are more resistant to degradation.

In a preferred embodiment of the landfarming experiment, the chamber shape is cylindrical and the volume of the cylinder is approximately 2,749 cubic centimeters. Preferably, eight containers are used. Each two containers preferably receives one of the following concentrations of oily sludge in soil: 3.5, 7.0, 10.5, and 14.0% (wt/wt). Each container preferably receives approximately 200 grams of soil mixed with oily sludge according to its application rate, water, and fixed amounts of nutrients (organic fertilizer, 1% w/w). The degree of degradation is determined using the ratios of n-C17 to pristane and n-C18 to phytane. The chromatographic isoprenoids and the ratio of n-C17/Pr and n-C18/Ph for the landfarming experiment sludge samples are listed in Table 1 herein. The desired concentration of components resulting from the landfarming experiment can vary widely depending on many factors such as oily sludge composition, treatment time, nutrients available for oily degrading bacteria to consume hydrocarbons, etc.

TABLE 1

Chromatographic peak area counts for C17 and C18 n-alkanes and for pristine and phytane isoprenoids of landfarming experiment sludge samples

| Oily sludge application rate %, w/w | Date sampled | $nC_{17}/Pr$ | $nC_{18}/Ph$ | $nC_{17}$ | Pristane | $nC_{18}$ | Phytane |
|---|---|---|---|---|---|---|---|
| 3.5 | Apr. 21, 2002* | 2.49 | 1.31 | 268.90 | 108.20 | 334.60 | 256.03 |
|  | May 14, 2002 | 3.49 | 1.93 | 106.15 | 30.46 | 156.83 | 81.18 |
|  | Jun. 13, 2002 | 2.83 | 1.83 | 19.83 | 7.00 | 40.63 | 22.21 |
|  | Aug. 26, 2002 | 2.60 | 1.72 | 26.20 | 10.07 | 56.86 | 33.07 |
| 7.0 | Apr. 21, 2002* | 2.33 | 1.32 | 132.69 | 56.84 | 188.73 | 142.60 |
|  | May 14, 2002 | 3.21 | 1.66 | 70.72 | 22.05 | 125.71 | 75.76 |
|  | Jun. 13, 2002 | 2.85 | 1.78 | 20.33 | 7.13 | 43.37 | 24.40 |
|  | Aug. 26, 2002 | 2.36 | 1.55 | 22.52 | 9.55 | 55.02 | 35.43 |
| 10.5 | Apr. 21, 2002* | 2.07 | 1.20 | 88.81 | 42.82 | 117.31 | 97.51 |
|  | May 14, 2002 | 3.26 | 1.45 | 96.34 | 29.58 | 126.24 | 86.83 |
|  | Jun. 13, 2002 | 2.52 | 1.48 | 31.34 | 12.42 | 67.82 | 45.74 |
|  | Aug. 26, 2002 | 2.10 | 1.36 | 36.52 | 17.36 | 79.52 | 58.26 |
| 14.0 | Apr. 21, 2002* | 2.13 | 1.22 | 28.45 | 13.34 | 36.50 | 29.85 |
|  | May 14, 2002 | 2.72 | 1.38 | 86.76 | 31.85 | 128.33 | 93.04 |
|  | Jun. 13, 2002 | 2.37 | 1.31 | 49.83 | 21.04 | 88.64 | 67.78 |
|  | Aug. 26, 2002 | 2.19 | 1.35 | 40.33 | 18.41 | 80.60 | 59.60 |

*Original sample

While the invention has been shown or described in only some of its forms, it should be apparent to those skilled in the art that it is not so limited, but is susceptible to various changes without departing from the scope of the invention.

We claim:

1. An apparatus for simulating environmental conditions in order to study the effect of the conditions on a specimen, the apparatus comprising:
   a chamber having one or more specimen containers contained therein, wherein at least one specimen container contains a soil specimen having oily sludge hydrocarbons;
   a heat source for providing heat in the chamber to simulate environmental conditions; and
   an air source for providing an air supply in the chamber to simulate environmental conditions such that degradation of the oily sludge hydrocarbons is initiated.

2. The apparatus of claim 1, further comprising a pressure regulator for regulating air pressure of the apparatus.

3. The apparatus of claim 1, further comprising a solenoid valve for controlling an automatic opening and closing of the air supply to the apparatus.

4. The apparatus of claim 1, further comprising a temperature indicator for displaying the present temperature in the apparatus.

5. The apparatus of claim 1, further comprising a control valve for controlling the flow of the air supply to the apparatus.

6. The apparatus of claim 1, further comprising a timer for controlling the timing of the air supply to the apparatus.

7. The apparatus of claim 1, further comprising a plurality of air dampers for regulating the air supply to the apparatus.

8. The apparatus of claim 1, further comprising a temperature controller for automatically controlling the temperature in the apparatus.

9. The apparatus of claim 1, wherein the environmental conditions capable of being simulated comprise temperature, wind, humidity, sunrays, and acid rain.

10. A method of simulating environmental conditions in order to study the effect of the conditions on a specimen, the method comprising the steps of:

positioning one or more specimen containers within a chamber, wherein at least one specimen container contains a soil specimen having oily sludge hydrocarbons;

utilizing a heat source to supply heat within the chamber to simulate temperature conditions on the soil specimen;

utilizing an air source to supply air within the chamber to simulate wind conditions on the soil specimen such that the oily sludge hydrocarbon is subject to degradation; and extracting the oily sludge hydrocarbons from the soil specimen in order to measure degradation of the oily sludge hydrocarbons.

11. The method of claim 10, further comprising a water source to simulate environmental conditions.

12. The method of claim 10, wherein the method is performed in a landfarming system.

* * * * *